United States Patent
Donno et al.

(10) Patent No.: US 9,173,744 B2
(45) Date of Patent: Nov. 3, 2015

(54) FEMORAL PROSTHESIS WITH MEDIALIZED PATELLAR GROOVE

(75) Inventors: Cosimo Donno, Pfungen (CH); Adam D. Henderson, Winterhur (CH)

(73) Assignee: Zimmer GMBH, Winterthur (CH)

( * ) Notice: Subject to any disclaimer, the term of this patent is extended or adjusted under 35 U.S.C. 154(b) by 0 days.

(21) Appl. No.: 13/819,528

(22) PCT Filed: Sep. 9, 2011

(86) PCT No.: PCT/EP2011/004556
§ 371 (c)(1),
(2), (4) Date: May 13, 2013

(87) PCT Pub. No.: WO2012/031774
PCT Pub. Date: Mar. 15, 2012

(65) Prior Publication Data
US 2013/0226305 A1   Aug. 29, 2013

Related U.S. Application Data

(60) Provisional application No. 61/381,803, filed on Sep. 10, 2010.

(51) Int. Cl.
*A61F 2/38* (2006.01)
*A61F 2/30* (2006.01)

(52) U.S. Cl.
CPC ............. *A61F 2/3859* (2013.01); *A61F 2/3877* (2013.01); *A61F 2002/30616* (2013.01); *A61F 2002/30892* (2013.01)

(58) Field of Classification Search
CPC ................ A61F 2/3859; A61F 2/3877; A61F 2002/30892; A61F 2002/3859; A61F 2002/3877; A61F 2002/3895; A61F 2002/38; A61F 2/38
USPC ............ 623/20.14, 20.15, 20.16, 20.17, 20.3, 623/20.31, 20.32, 20.35, 20.36
See application file for complete search history.

(56) References Cited

U.S. PATENT DOCUMENTS

| 4,081,866 A | 4/1978 | Upshaw et al. |
| 4,340,978 A | 7/1982 | Buechel et al. |

(Continued)

FOREIGN PATENT DOCUMENTS

| AU | 2006325787 B2 | 10/2013 |
| CN | 101330883 B | 3/2013 |

(Continued)

OTHER PUBLICATIONS

"Answer filed Dec. 1, 2010 of Zimmer, Inc and Zimmer Technology, Inc", *W. Norman Scott and Giles R Scuderi vs. Zimmer, Inc and Zimmer Technology, Inc* in the US District Court of Delaware in Case No. 10-772-GMS, (Dec. 1, 2010), 36 pgs.

(Continued)

*Primary Examiner* — Alvin Stewart
(74) *Attorney, Agent, or Firm* — Schwegman Lundberg & Woessner, P.A.

(57) ABSTRACT

A prosthetic femoral component (10) for an orthopaedic prosthesis has a canted patellar groove adapted for optimal patella/component interaction, with the component configured to have a medial or lateral cant depending upon the method of implantation. The femoral component defines a distal "component transverse plane," which is a plane tangent to the distal-most points of the component condyles (12,14). In a "mechanical" implantation, the component transverse plane is substantially normal to the mechanical femoral axis of the femur after the component has been implanted. Where the femoral component is configured to be "mechanically oriented" in this manner, the component has a medially canted patellar groove. On the other hand, an "anatomic" implantation is one in which, after the component has been implanted, the component transverse plane is substantially parallel to an "anatomic" transverse plane. The anatomic transverse plane is perpendicular to the anatomic axis of the femur from a sagittal view, and is inclusive of a line connecting the distal-most points of the natural femoral condyles before resection. Where the femoral component is configured to be "anatomically oriented" in this way, the component has a non-canted or slightly laterally canted patellar groove.

16 Claims, 4 Drawing Sheets

(56) References Cited

U.S. PATENT DOCUMENTS

| | | | |
|---|---|---|---|
| 4,662,889 A | 5/1987 | Zichner et al. | |
| 4,888,020 A * | 12/1989 | Horber | 623/20.35 |
| 4,944,756 A | 7/1990 | Kenna | |
| 5,061,271 A | 10/1991 | Van Zile | |
| 5,133,758 A | 7/1992 | Hollister | |
| 5,137,536 A | 8/1992 | Koshino | |
| 5,226,915 A | 7/1993 | Bertin | |
| 5,282,861 A | 2/1994 | Kaplan | |
| 5,326,361 A * | 7/1994 | Hollister | 623/20.31 |
| 5,445,642 A | 8/1995 | McNulty et al. | |
| 5,549,686 A | 8/1996 | Johnson et al. | |
| 5,549,688 A * | 8/1996 | Ries et al. | 623/20.35 |
| 5,609,643 A | 3/1997 | Colleran et al. | |
| 5,681,354 A * | 10/1997 | Eckhoff | 623/20.35 |
| 5,688,279 A | 11/1997 | McNulty et al. | |
| 5,728,162 A | 3/1998 | Eckhoff | |
| 5,776,201 A | 7/1998 | Colleran et al. | |
| 5,824,105 A * | 10/1998 | Ries et al. | 623/20.31 |
| 5,871,546 A | 2/1999 | Colleran et al. | |
| 5,935,173 A | 8/1999 | Roger et al. | |
| 6,013,103 A | 1/2000 | Kaufman et al. | |
| 6,039,764 A | 3/2000 | Pottenger et al. | |
| 6,152,960 A * | 11/2000 | Pappas | 623/20.31 |
| 6,197,064 B1 | 3/2001 | Haines et al. | |
| 6,217,619 B1 * | 4/2001 | Keller | 623/20.34 |
| 6,235,060 B1 * | 5/2001 | Kubein-Meesenburg et al. | 623/20.31 |
| 6,264,697 B1 | 7/2001 | Walker | |
| 6,325,828 B1 * | 12/2001 | Dennis et al. | 623/20.14 |
| 6,364,911 B1 * | 4/2002 | Schmotzer et al. | 623/20.31 |
| 6,540,786 B2 | 4/2003 | Chibrac et al. | |
| 6,540,787 B2 | 4/2003 | Biegun et al. | |
| 6,589,283 B1 * | 7/2003 | Metzger et al. | 623/20.35 |
| 6,616,696 B1 | 9/2003 | Merchant | |
| 6,699,291 B1 | 3/2004 | Augoyard et al. | |
| 6,712,856 B1 | 3/2004 | Carignan et al. | |
| 6,770,099 B2 * | 8/2004 | Andriacchi et al. | 623/20.35 |
| 6,802,865 B2 | 10/2004 | Biegun et al. | |
| 6,846,329 B2 * | 1/2005 | McMinn | 623/20.14 |
| 6,893,467 B1 | 5/2005 | Bercovy | |
| 7,081,137 B1 | 7/2006 | Servidio | |
| 7,306,609 B2 | 12/2007 | Schmotzer et al. | |
| 7,364,590 B2 * | 4/2008 | Siebel | 623/20.35 |
| 7,413,577 B1 | 8/2008 | Servidio | |
| 7,678,152 B2 * | 3/2010 | Suguro et al. | 623/20.27 |
| 7,695,520 B2 | 4/2010 | Metzger et al. | 623/20.35 |
| 7,806,897 B1 * | 10/2010 | Bonutti | 606/86 R |
| 8,062,377 B2 | 11/2011 | Haines | |
| 8,075,626 B2 * | 12/2011 | Dun | 623/20.27 |
| 8,088,167 B2 | 1/2012 | Haines | |
| 8,298,288 B2 * | 10/2012 | Walker | 623/20.21 |
| 8,357,202 B2 * | 1/2013 | Heggendorn et al. | 623/20.14 |
| 8,377,141 B2 * | 2/2013 | McMinn | 623/20.35 |
| 8,394,147 B2 * | 3/2013 | Otto et al. | 623/20.14 |
| 8,409,293 B1 * | 4/2013 | Howard et al. | 623/20.15 |
| 8,480,753 B2 * | 7/2013 | Collazo et al. | 623/20.35 |
| 8,480,754 B2 * | 7/2013 | Bojarski et al. | 623/20.35 |
| 8,500,816 B2 * | 8/2013 | Dees et al. | 623/20.14 |
| 8,551,179 B2 | 10/2013 | Jones et al. | |
| 8,721,732 B2 * | 5/2014 | Samuelson et al. | 623/20.35 |
| 2003/0158606 A1 | 8/2003 | Coon et al. | |
| 2003/0225458 A1 | 12/2003 | Donkers et al. | |
| 2004/0039450 A1 | 2/2004 | Griner et al. | |
| 2004/0172137 A1 | 9/2004 | Blaylock et al. | |
| 2004/0249467 A1 | 12/2004 | Meyers et al. | |
| 2005/0102032 A1 | 5/2005 | Beynnon et al. | |
| 2005/0107884 A1 | 5/2005 | Johnson et al. | |
| 2005/0177169 A1 | 8/2005 | Fisher et al. | |
| 2005/0283249 A1 | 12/2005 | Carson | |
| 2005/0283250 A1 | 12/2005 | Coon et al. | |
| 2005/0283251 A1 | 12/2005 | Coon et al. | |
| 2005/0283252 A1 | 12/2005 | Coon et al. | |
| 2005/0283253 A1 | 12/2005 | Coon et al. | |
| 2006/0028773 A1 | 2/2006 | Shimazawa et al. | |
| 2006/0129246 A1 | 6/2006 | Steffensmeier | |
| 2006/0224244 A1 | 10/2006 | Thomas et al. | |
| 2006/0235541 A1 | 10/2006 | Hodorek | |
| 2006/0235542 A1 | 10/2006 | Hodorek et al. | |
| 2006/0287733 A1 | 12/2006 | Bonutti | |
| 2007/0088444 A1 | 4/2007 | Hodorek et al. | |
| 2007/0123984 A1 | 5/2007 | Hodorek | |
| 2007/0135926 A1 * | 6/2007 | Walker | 623/20.31 |
| 2007/0179607 A1 | 8/2007 | Hodorek et al. | |
| 2007/0233269 A1 | 10/2007 | Steines et al. | |
| 2007/0260323 A1 * | 11/2007 | Earl et al. | 623/20.35 |
| 2008/0058947 A1 | 3/2008 | Earl et al. | |
| 2008/0058948 A1 | 3/2008 | Biegun et al. | |
| 2008/0097616 A1 | 4/2008 | Meyers et al. | |
| 2008/0119940 A1 | 5/2008 | Otto et al. | |
| 2008/0140212 A1 | 6/2008 | Metzger et al. | |
| 2008/0188855 A1 | 8/2008 | Brown et al. | |
| 2008/0188937 A1 | 8/2008 | Ribic | |
| 2008/0188942 A1 | 8/2008 | Brown et al. | |
| 2008/0243258 A1 | 10/2008 | Sancheti | |
| 2008/0281428 A1 | 11/2008 | Meyers et al. | |
| 2008/0288080 A1 | 11/2008 | Sancheti | |
| 2009/0036992 A1 | 2/2009 | Tsakonas | |
| 2009/0043395 A1 | 2/2009 | Hotokebuchi et al. | |
| 2009/0062924 A1 | 3/2009 | Kito et al. | |
| 2009/0105772 A1 | 4/2009 | Seebeck et al. | |
| 2009/0132055 A1 * | 5/2009 | Ferro | 623/20.21 |
| 2009/0222103 A1 | 9/2009 | Fitz et al. | |
| 2009/0265011 A1 | 10/2009 | Mandell | |
| 2009/0265013 A1 | 10/2009 | Mandell | |
| 2009/0306785 A1 | 12/2009 | Samuelson | |
| 2009/0306787 A1 | 12/2009 | Crabtree et al. | |
| 2009/0319047 A1 | 12/2009 | Walker | |
| 2009/0319048 A1 * | 12/2009 | Shah et al. | 623/20.29 |
| 2009/0319049 A1 * | 12/2009 | Shah et al. | 623/20.31 |
| 2009/0326663 A1 | 12/2009 | Dun | |
| 2009/0326665 A1 | 12/2009 | Wyss et al. | |
| 2009/0326666 A1 | 12/2009 | Wyss et al. | |
| 2009/0326667 A1 | 12/2009 | Williams et al. | |
| 2010/0036992 A1 | 2/2010 | Pinskerova | |
| 2010/0036500 A1 | 2/2010 | Heldreth et al. | |
| 2010/0042224 A1 | 2/2010 | Otto et al. | |
| 2010/0161067 A1 | 6/2010 | Saleh et al. | |
| 2010/0191298 A1 | 7/2010 | Earl et al. | |
| 2010/0305708 A1 | 12/2010 | Lang | |
| 2010/0329530 A1 | 12/2010 | Lang et al. | |
| 2011/0022179 A1 | 1/2011 | Andriacchi et al. | |
| 2011/0093083 A1 | 4/2011 | Earl et al. | |
| 2011/0144760 A1 | 6/2011 | Wong et al. | |
| 2011/0218541 A1 | 9/2011 | Bailey et al. | |
| 2011/0307067 A1 | 12/2011 | Dees | |
| 2012/0203350 A1 * | 8/2012 | Hagen et al. | 623/20.22 |
| 2012/0310362 A1 * | 12/2012 | Li et al. | 623/20.32 |
| 2012/0323334 A1 | 12/2012 | Jones et al. | |
| 2012/0323335 A1 | 12/2012 | Parisi et al. | |
| 2012/0323336 A1 | 12/2012 | Parisi et al. | |
| 2012/0323337 A1 | 12/2012 | Parisi et al. | |
| 2013/0006370 A1 | 1/2013 | Wogoman et al. | |
| 2013/0006371 A1 | 1/2013 | Wogoman et al. | |
| 2013/0006376 A1 | 1/2013 | Wogoman et al. | |
| 2013/0006378 A1 | 1/2013 | Wogoman | |
| 2013/0035765 A1 * | 2/2013 | Dacus | 623/20.31 |
| 2013/0197653 A1 * | 8/2013 | Hawkins et al. | 623/20.27 |
| 2013/0226305 A1 * | 8/2013 | Donno et al. | 623/20.35 |
| 2014/0128973 A1 * | 5/2014 | Howard et al. | 623/14.12 |
| 2014/0142713 A1 * | 5/2014 | Wright et al. | 623/20.21 |

FOREIGN PATENT DOCUMENTS

| | | |
|---|---|---|
| CN | 103732186 A | 4/2014 |
| DE | 202007014128 U1 | 1/2008 |
| EP | 0303467 A2 | 2/1989 |
| EP | 0376658 B1 | 6/1994 |
| EP | 0381352 B1 | 6/1994 |
| EP | 0567705 B1 | 7/1997 |
| EP | 0993812 A2 | 4/2000 |
| EP | 1013232 A2 | 6/2000 |
| EP | 1285638 A2 | 2/2003 |
| EP | 1033117 B1 | 6/2004 |
| EP | 0975286 B1 | 8/2004 |

(56) References Cited

FOREIGN PATENT DOCUMENTS

| | | |
|---|---|---|
| EP | 1477142 A2 | 11/2004 |
| EP | 1477143 A1 | 11/2004 |
| EP | 1285638 B1 | 11/2005 |
| EP | 1719478 A2 | 11/2006 |
| EP | 1722721 A1 | 11/2006 |
| EP | 1354571 B1 | 6/2007 |
| EP | 1862150 A1 | 12/2007 |
| EP | 2004099 A2 | 12/2008 |
| EP | 1867302 B1 | 9/2009 |
| EP | 2147660 A1 | 1/2010 |
| EP | 2158878 A1 | 3/2010 |
| EP | 1555962 B1 | 2/2011 |
| EP | 2324799 A2 | 5/2011 |
| EP | 2335654 A1 | 6/2011 |
| FR | 2901996 A1 | 12/2007 |
| JP | 3267055 A | 11/1991 |
| JP | 0553501 A | 3/1993 |
| JP | 0568987 A | 3/1993 |
| JP | 9149908 A | 6/1997 |
| JP | 11504226 A | 4/1999 |
| JP | 11511347 A | 10/1999 |
| JP | 3469972 B2 | 11/2003 |
| JP | 3495161 B2 | 2/2004 |
| JP | 2004166802 A | 6/2004 |
| JP | 2005532089 A | 10/2005 |
| JP | 2009519781 A | 5/2009 |
| JP | 4820547 B2 | 11/2011 |
| JP | 5571863 B1 | 7/2014 |
| JP | 2014522292 A | 9/2014 |
| WO | WO-9535074 A1 | 12/1995 |
| WO | WO-9603939 A1 | 2/1996 |
| WO | WO-0023010 A1 | 4/2000 |
| WO | WO-03094782 A2 | 11/2003 |
| WO | WO-2004016204 A1 | 2/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2007054553 A1 | 5/2007 |
| WO | WO-2007109641 A2 | 9/2007 |
| WO | WO-2008054389 A1 | 5/2008 |
| WO | WO-2009088234 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010108550 A1 | 9/2010 |
| WO | WO-2011072235 A2 | 6/2011 |
| WO | WO-2012031774 A1 | 3/2012 |
| WO | WO-2012112698 A2 | 8/2012 |
| WO | WO-2012173704 A1 | 12/2012 |
| WO | WO-2012173706 A1 | 12/2012 |
| WO | WO-2012173740 A1 | 12/2012 |

OTHER PUBLICATIONS

"U.S. Appl. No. 11/611,021, Non-Final Office Action mailed Dec. 7, 2009", 4 pgs.
"U.S. Appl. No. 11/611,021, Final Office Action mailed Mar. 10, 2011", 7 pgs.
"U.S. Appl. No. 11/611,021, Non Final Office Action mailed Jul. 21, 2010", 8 pgs.
"U.S. Appl. No. 11/611,021, Response filed May 3, 2010 to Non Final Office Action mailed Dec. 7, 2009", 14 pgs.
"U.S. Appl. No. 11/611,021, Response filed Dec. 21, 2010 to Non Final Office Action mailed Jul. 21, 2010", 14 pgs.
"U.S. Appl. No. 11/780,248, Non Final Office Action mailed Feb. 4, 2010", 4 pgs.
"U.S. Appl. No. 11/780,248, Non Final Office Action mailed Jul. 21, 2010", 11 pgs.
"U.S. Appl. No. 11/780,248, Response filed May 3, 2010 to Non Final Office Action mailed Feb. 4, 2010", 13 pgs.
"U.S. Appl. No. 12/974,018, Final Office Action mailed Apr. 13, 2012", 11 pgs.
"U.S. Appl. No. 12/974,018, Non Final Office Action mailed Nov. 10, 2011", 5 pgs.
"U.S. Appl. No. 12/974,018, Preliminary Amendment filed Dec. 21, 2010", 4 pgs.
"U.S. Appl. No. 12/974,018, Response filed Mar. 8, 2012 to Non Final Office Action mailed Nov. 10, 2011", 12 pgs.
"U.S. Appl. No. 12/974,018, Response filed Oct. 12, 2012 to Final Office Action mailed Apr. 13, 2012", 16 pgs.
"U.S. Appl. No. 13/161,624, Notice of Allowance mailed Mar. 12, 2013", 11 pgs.
"U.S. Appl. No. 13/161,624, Response filed Feb. 26, 2013 to Restriction Requirement mailed Sep. 26, 2012", 9 pgs.
"U.S. Appl. No. 13/161,624, Restriction Requirement mailed Sep. 26, 2012", 8 pgs.
"U.S. Appl. No. 13/459,060, Preliminary Amendment filed Apr. 27, 2012", 6 pgs.
"U.S. Appl. No. 13/459,061, Preliminary Amendment filed Apr. 27, 2012", 6 pgs.
"U.S. Appl. No. 13/459,064, Preliminary Amendment filed Apr. 27, 2012", 6 pgs.
"Australian Application Serial No. 2006325787, Office Action mailed Mar. 14, 2012", 2 pgs.
"Australian Application Serial No. 2006325787, Office Action mailed Nov. 14, 2011", 2 pgs.
"Australian Application Serial No. 2006325787, Response filed May 3, 2013 to Office Action mailed Mar. 14, 2012", 10 pgs.
"Australian Application Serial No. 2006325787, Response filed Feb. 21, 2012 to Office Action mailed Nov. 14, 2011", 34 pgs.
"Chinese Application Serial No. 200680046893, Office Action mailed Aug. 3, 2012", (W/ English Translation), 8 pgs.
"Chinese Application Serial No. 200680046893, Office Action mailed Aug. 10, 2010", (W/ English Translation), 22 pgs.
"Chinese Application Serial No. 200680046893, Office Action mailed Dec. 6, 2011", (W/ English Translation), 5 pgs.
"Chinese Application Serial No. 200680046893, Response filed Jan. 23, 2012 to Office Action mailed Dec. 6, 2011", (W/ English Translation), 11 pgs.
"Chinese Application Serial No. 200680046893.7, Response filed Oct. 17, 2012 to Office Action mailed Aug. 3, 2012", (W/ English Translation), 8 pgs.
"Complaint of W. Norman Scot and Giles R. Scuderi filed Sep. 9, 2010", *W. Norman Scott and Giles R Scuderi* vs. *Zimmer, Inc and Zimmer Technology, Inc* in the US District Court of Delaware in Case No. 10-772-GMS, (Sep. 9, 2010), 24 pgs.
"Extramedullary/Intramedullary Tibial Resector: Surgical Technique", Nexgen Complete Knee Solution, Zimmer, Inc. 97-5997-02 Rev 1, (2000, 2002), 25 pgs.
"Gender Solutions Natural-Knee Flex System", Zimmer, Inc., (2007, 2009), 6 pgs.
"Gender Solutions Natural-Knee Flex System: Surgical Technique", Zimmer, Inc., (2007, 2008, 2009), 36 pgs.
"Gender Solutions Patello-Femoral Joint (PFJ) System: Surgical Technique", Zimmer Inc., (2008, 2009), 38 pgs.
"International Application Serial No. PCT/US2012/035688, Partial Search Report mailed Jul. 3, 2012", 8 pgs.
"International Application Serial No. PCT/US2012/035688, Search Report mailed Sep. 17, 2012", 7 pgs.
"International Application Serial No. PCT/US2012/035688, Written Opinion mailed Sep. 17, 2012", 11 pgs.
"International Application Serial No. PCT/US2012/035691, Partial Search Report mailed Jul. 10, 2012", 8 pgs.
"International Application Serial No. PCT/US2012/035691, Search Report mailed Sep. 17, 2012", 7 pgs.
"International Application Serial No. PCT/US2012/035691, Written Opinion mailed Sep. 17, 2012", 11 pgs.
"International Application Serial No. PCT/US2012/035693, Partial Search Report mailed Jun. 27, 2012", 8 pgs.
"International Application Serial No. PCT/US2012/035693, Search Report mailed Oct. 9, 2012", 7 pgs.
"International Application Serial No. PCT/US2012/035693, Written Opinion mailed Oct. 9, 2012", 11 pgs.
"International Application Serial No. PCT/US2012/038531, Search Report mailed Oct. 8, 2012", 14 pgs.

(56) References Cited

OTHER PUBLICATIONS

"International Application Serial No. PCT/US2012/038531, Written Opinion mailed Oct. 8, 2012", 10 pgs.

"Japanese Application Serial No. 2008-545981, Examiners Decision of Final Refusal mailed Oct. 16, 2012", (W/ English Translation), 3 pgs.

"Japanese Application Serial No. 2008-545981, Office Action mailed Apr. 17, 2012", (W/ English Translation), 5 pgs.

"Japanese Application Serial No. 2008-545981, Office Action mailed Jul. 5, 2011", (W/ English Translation), 13 pgs.

"Japanese Application Serial No. 2008-545981, Response filed Oct. 5, 2011 to Office Action mailed Jul. 5, 2011", (W/ English Translation), 6 pgs.

"Japanese Application Serial No. 2008-545981, Response filed Aug. 30, 2012 to Office Action mailed Apr. 17, 2012", (W/ English Translation), 5 pgs.

"Japanese Application Serial No. 2011-221305, Office Action mailed Feb. 26, 2013", (W/ English Translation), 13 pgs.

"Japanese Application Serial No. 2011-221305, Office Action mailed Sep. 17, 2013", (W/ English Translation), 5 pgs.

"Japanese Application Serial No. 2011-221305, Response filed Aug. 26, 2013 to Office Action mailed Feb. 26, 2013", (W/ English Translation), 9 pgs.

"LPS-Flex Fixed Bearing Knee: Surgical Technique", Zimmer, Inc., (2004, 2007, 2008), 16 pgs.

"NexGen Implant Options Surgeon-Specific", Zimmer Inc., 16 pgs.

"NexGen LPS Fixed Knee: Surgical Technique", Zimmer Inc., (2002, 2008), 44 pgs.

"NexGen LPS-Flex Mobile and LPS-Mobile Bearing Knees", Zimmer, Inc., (2007, 2008), 4 pgs.

"Surgical Technique for the CR-Flex Fixed Bearing Knee", NexGen Complete Knee Solution, Zimmer, Inc., (2003), 22 pgs.

"Unicompartmental High Flex Knee: Intramedullary, Spacer Block Option and Extramedullary Minimally Invasive Surgical Techniques", Zimmer, Inc., (2004, 2009, 2010), 62 pgs.

Hitt, Kirby, et al., "Anthropometric Measurements of the Human Knee: Correlation to the Sizing of Current Knee Arthroplasty Systems", The Journal of Bone & Joint Surgery, (2003), 114-122.

Mensch, Joseph S, et al., "Knee Morphology as a Guide to Knee Replacement", Clinical Orthopaedics and Related Research No. 112, (Oct. 1975), 231-241.

Poilvache, Pascal L, et al., "Rotational Landmarks and Sizing of the Distal Femur in Total Knee Arthroplasty", Clinical Orthopaedics and Related Research, No. 331, (1996), 35-46.

Seedhom, B B, et al., "Dimensions of the Knee—Radiographic and Autopsy Study of Sizes Required for a Knee Prosthesis", Annals of the Rheumatic Diseases, (1972), 54-58.

Yoshioka, Yuki, et al., "The Anatomy and Functional Axes of the Femur", The Journal of Bone and Joint Surgery, vol. 69A, No. 6, (Jul. 1987), 873-880.

"International Application Serial No. PCT/EP2011/004556, International Preliminary Report on Patentability mailed Mar. 12, 2013", 9 pgs.

"International Application Serial No. PCT/EP2011/004556, International Search Report mailed Feb. 9, 2012", 6 pgs.

"International Application Serial No. PCT/EP2011/004556, Written Opinion mailed Mar. 12, 2013", 9 pgs.

"U.S. Appl. No. 11/611,021, Non Final Office Action mailed Jan. 17, 2014", 11 pgs.

"U.S. Appl. No. 12/974,018, Non Final Office Action mailed Apr. 4, 2014", 11 pgs.

"U.S. Appl. No. 13/459,060, Non Final Office Action mailed Mar. 14, 2014", 8 pgs.

"U.S. Appl. No. 13/459,060, Response filed Jan. 3, 2014 to Restriction Requirement mailed Nov. 4, 2013", 25 pgs.

"U.S. Appl. No. 13/459,060, Restriction Requirement mailed Nov. 4, 2013", 6 pgs.

"U.S. Appl. No. 61/381,803, filed Sep. 10, 2010", 23 pgs.

"Australian Application Serial No. 2012271153, Amendment filed Jan. 16, 2014", 13 pgs.

"Canadian Application Serial No. 2,641,966, Office Action mailed Jul. 16, 2013", 2 pgs.

"Canadian Application Serial No. 2,641,966, Response filed Jan. 15, 2014 to Office Action mailed Jul. 16, 2013", 6 pgs.

"European Application Serial No. 06840269.2, Examination Notification Art. 94(3) mailed Jan. 24, 2014", 6 pgs.

"International Application Serial No. PCT/US2012/035693, International Preliminary Report on Patentability mailed Jan. 3, 2014", 13 pgs.

"Japanese Application Serial No. 2011-221305, Response filed Dec. 17, 2013 to Office Action mailed Sep. 17, 2013", (W/ English Translation of Claims), 8 pgs.

"U.S. Appl. No. 11/611,021, Final Office Action mailed Sep. 25, 2014", 9 pgs.

"U.S. Appl. No. 11/611,021, Preliminary Amendment filed Oct. 26, 2007", 7 pgs.

"U.S. Appl. No. 11/611,021, Response filed Jul. 15, 2014 to Non-Final Office Action dated Jan. 17, 2014", 19 pgs.

"U.S. Appl. No. 12/974,018, Final Office Action mailed Oct. 10, 2014", 12 pgs.

"U.S. Appl. No. 12/974,018, Response filed Jul. 30, 2014 to Non-Final Office Action mailed Apr. 4, 2014", 15 pgs.

"U.S. Appl. No. 13/459,060, Non Final Office Action mailed Oct. 9, 2014", 11 pgs.

"U.S. Appl. No. 13/459,060, Response filed Jul. 14, 2014 to Non-Final Office Action mailed Mar. 14, 2014", 30 pgs.

"Canadian Application Serial No. 2,641,966, Office Action mailed Feb. 6, 2014", 2 pgs.

"Canadian Application Serial No. 2,641,966, Office Action mailed Aug. 25, 2014", 2 pgs.

"European Application Serial No. 06840269.2, Examination Notification Art. 94(3) mailed Nov. 12, 2014", 4 pgs.

"Japanese Application Serial No. 2014-515821, Request for Examination Amendment filed Apr. 8, 2014", (W/ English Translation), 18 pgs.

"U.S. Appl. No. 11/611,021, Response filed Feb. 24, 2015 to Final Office Action mailed Sep. 25, 2014", 16 pgs.

"U.S. Appl. No. 12/974,018, Appeal Brief filed Feb. 20, 2015", 24 pgs.

"U.S. Appl. No. 13/459,060, Final Office Action mailed Apr. 1, 2015", 11 pgs.

"U.S. Appl. No. 13/459,060, Response filed Feb. 18, 2015 to Non-Final Office Action mailed Oct. 9, 2014", 23 pgs.

\* cited by examiner

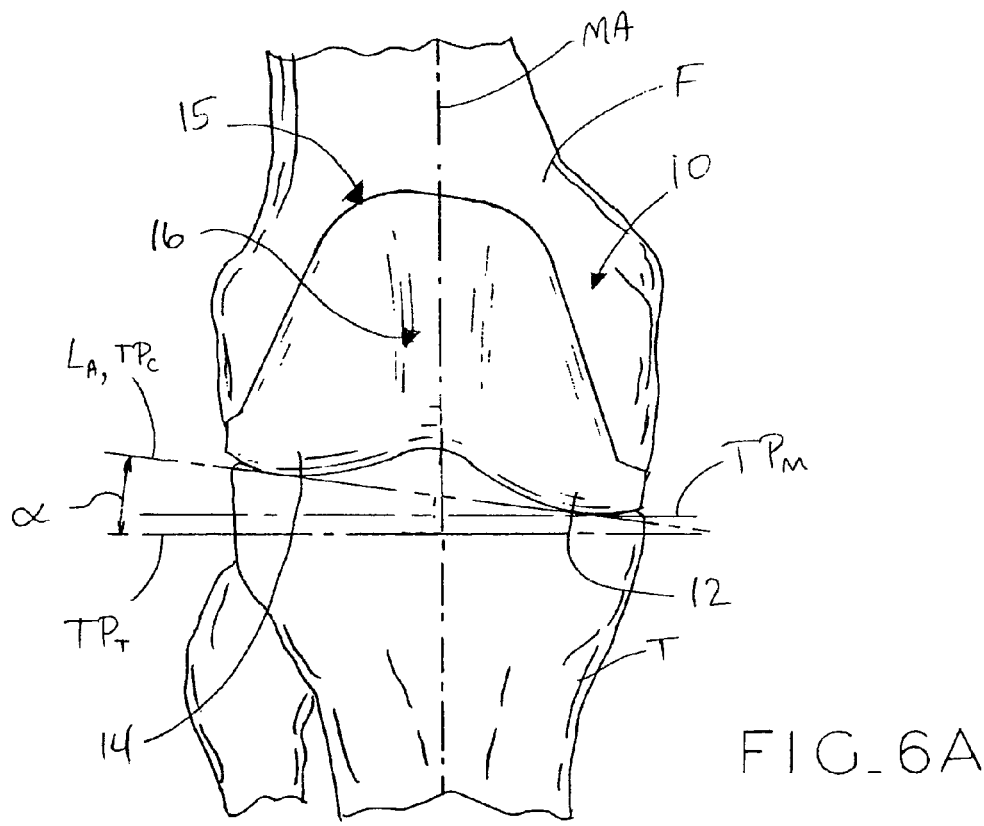
FIG_6A
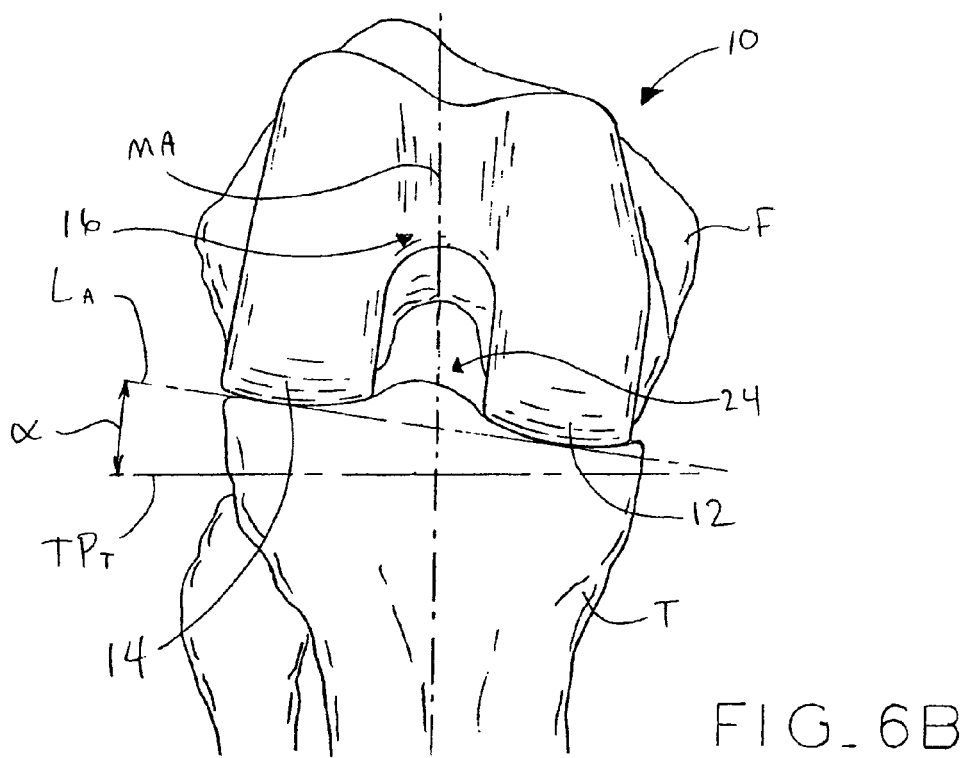
FIG_6B

FEMORAL PROSTHESIS WITH MEDIALIZED PATELLAR GROOVE

RELATED APPLICATION

This patent application is a U.S. National Stage Filing under 35 U.S.C. §371 of International Patent Application Serial No. PCT/EP2011/004556, filed on Sep. 9, 2011 and published on Mar. 15, 2012 as WO 2012/031774 A1, which claims the benefit of priority of U.S. Provisional Patent Application Ser. No. 61/381,803, filed on Sep. 10, 2010, the benefit of priority of each of which is claimed hereby and each of which is incorporated by reference herein in its entirety.

BACKGROUND

1. Technical Field

The present disclosure relates to orthopaedic prostheses and, more particularly, to femoral prosthetic components with enhanced patello-femoral articulation characteristics.

2. Description of the Related Art

Orthopaedic prostheses are commonly utilized to repair and/or replace damaged bone and tissue in the human body. For example, a knee prosthesis may include a femoral component which replaces the articular surface of one or both of the natural femoral condyles, and/or the natural femoral sulcus. The femoral sulcus (also referred to as a patellar or trochlear groove) articulates with the patella during flexion and extension of the knee.

In some partial knee arthroplasty (PKA) procedures, natural bone may only be resected in the area of the patellar groove, and a prosthetic femoral sulcus component may be inserted in place of the resected bone for articulation with a natural or prosthetic patella. In a total knee arthroplasty (TKA) procedure, anterior, distal, and posterior portions of the natural femur are resected. A knee prosthesis including distal and posterior condyles, joined together by an anterior patellar flange, is then installed in place of the resected bone. In a TKA procedure, the patellar flange includes a prosthetic patellar groove.

A common goal of PKA and TKA procedures is to reproduce natural knee kinematics using the associated prosthetic components and, more generally, to produce kinematic characteristics of the knee prosthesis that promote favorable patient outcomes including minimized pain, enhanced biomechanical efficiency, reproduction of intact knee Patello-Femoral (PF) and Tibio-Femoral (TF) kinematics, short recovery times, decreased risk of joint subluxation, and long prosthetic component surface lives. To these ends, substantial design efforts have focused on providing prosthetic components which account for differences in natural bone structure and joint kinematics among various patient groups, such as gender, ethnicity, patient size, and the like. Other considerations which figure into the design and function of prosthetic knee components include balancing of soft tissue (i.e., ligaments, tendons and the like) near the prosthetic components, special articulation characteristics of the knee such as internal/external rotation and femoral lateral rollback, and hyperextension and deep flexion considerations, for example.

Design efforts have included producing "asymmetric" femoral components for knee prostheses, in which a particular asymmetry of the component seeks to provide enhanced articular PF and TF characteristics. With respect to a patellar groove of such asymmetric components, a groove angled laterally upward with respect to a femoral mid-plane axis has previously been employed.

SUMMARY

The present disclosure provides an alternative prosthetic femoral component for an orthopaedic prosthesis with a canted patellar groove adapted for optimal patella/component interaction, in which the component is configurable with a medial or lateral cant depending upon the method of implantation.

The femoral component defines a distal "component transverse plane," which is a plane tangent to the distal-most points of the component condyles.

In a "mechanical" implantation, the component transverse plane is substantially normal to the mechanical femoral axis of the femur after the component has been implanted. Where the femoral component is configured to be "mechanically oriented" in this manner, the component has a medially canted patellar groove.

On the other hand, an "anatomic" implantation is one in which, after the component has been implanted, the component transverse plane is substantially parallel to an "anatomic" transverse plane. The anatomic transverse plane is perpendicular to the anatomic axis of the femur from a sagittal view, and is inclusive of a line connecting the distal-most points of the natural femoral condyles before resection. Where the femoral component is configured to be "anatomically oriented" in this way, the component has a non-canted or slightly laterally canted patellar groove.

The term "perpendicular," as used herein to describe the relationship between a plane and a line or axis, implies only a two-dimensional relationship in which the line forms a right angle to the plane from a particular perspective. Thus, an axis may be perpendicular to a plane in one perspective (i.e. as viewed when facing a sagittal plane), but may be angled from another perspective (i.e., as viewed when facing a coronal plane). In contrast, the term "normal," as used herein to describe the relationship between a plane and a line or axis, implies a three-dimensional relationship in which the line forms a right angle to the plane from all perspectives.

The present disclosure is based on the general concept of orienting the patellar groove of the femoral component such that a reproduction of the natural femur morphology as well as of the natural knee PF and TF kinematics is sought, and that at the same time the implantation method, i.e. "mechanical" or "anatomic", is taken into account. Specifically, the implantation method-dependent orientation of the patellar groove according to the present disclosure aligns the femoral component advantageously with the femoral head of the femur. In particular, a patellar axis (as defined below) may be approximately oriented such that the patellar axis lies in a plane which goes through the femoral head, in particular thereby at least approximately intersecting the geometric center of the femoral head. Stated another way, the patellar axis "aims" or "points" toward the center of the femoral head. In order to achieve this aim, the orientation of the patellar groove, and in particular the cant of a suitably defined patellar axis, may be chosen depending on the respective method of implantation.

In use, a component having a patellar axis adapted to point toward the center of femoral head 7 is implanted upon an appropriately resected surface, in which the choice of component and the choice of resection technique cooperate to ensure that the patellar axis will be properly oriented (e.g., within plus-or-minus 2 to 3 degrees) toward the center of head 7. To find the center of femoral head 7, the surgeon may move the patient's leg through a wide range of motion, while palpating the femoral head through the skin. Based on the detected movement of femoral head 7, the surgeon can estimate the size and location of femoral head 7 and therefore can estimate the location of the center of femoral head 7. Alternatively, a surgeon may use pre-operative imagine (discussed above) to visually estimate the location of the center of femoral head 7.

By providing a femoral component made in accordance with the present disclosure and implanting such femoral component as described herein, it is possible for the first time for such femoral components to compensate for the effect of the so-called "external rotation" of the femur (external rotation being a phenomenon that is well-known in the art). More particularly, the patellar groove of a femoral component may be oriented with respect to the femoral head, taking into account the implantation method intended for that femoral component, such that the femoral component accommodates the "external rotation" of the femur. Advantageously, this accommodation promotes natural PF and TF knee kinematics.

In the illustrated embodiments of the disclosure, the varus/valgus angle, or "knee inclination" measured in a coronal plane, is taken to be equal to the internal/external rotation angle of the knee, as measured in a transverse plane. Moreover, the femoral prosthesis and associated bone resections may cooperate to preserve this angular equality throughout the range of flexion, such that the femoral component promotes balanced ligament tension throughout the range of motion.

In one form thereof, the present invention provides a femoral component adapted to mount to a femur, the femur defining a mechanical axis and an anatomic axis, the component having a bone-contacting surface and an opposed articulation surface, the component further having proximal, distal, anterior and posterior portions, the component comprising: a pair of condyles including a medial condyle and a lateral condyle, each of the condyles defining respective distal-most points and posterior-most points; a patellar groove proximate the anterior portion of the component; a transverse plane tangent to each of the distal-most points of the condyles; a coronal plane perpendicular to the transverse plane and tangent to at least one of the posterior-most points of the condyles; a sagittal plane perpendicular to the transverse plane and disposed between the lateral condyle and the medial condyle, the sagittal plane inclusive of a distal-most point of the patellar groove, the sagittal plane including a component midline that is normal to the transverse plane and inclusive of the distal-most point of the patellar groove, the patellar groove defining a medially canted patellar axis when viewed from an anterior side of the component, the patellar axis medially diverging from the component midline as the patellar axis extends proximally to define a medially canted angle between the patellar axis and the component midline.

In another form thereof, the present invention provides a femoral component adapted to mount to a femur, the femur having a mechanical axis, an anatomic axis and medial and lateral condyles defining distal-most points, an anatomic transverse plane tangent to the distal-most points of the medial and lateral condyles of the femur, the component having a bone-contacting surface and an opposed articulation surface, the component comprising: a pair of condyles including a medial condyle and a lateral condyle, each of the condyles defining respective distal-most points when the component is mounted to the femur, the condyles further defining respective posterior-most points when the component is mounted to the femur; a transverse plane inclusive of a line connecting the distal-most points of the condyles, the transverse plane oriented to be parallel with the anatomic transverse plane when the component is mounted to the femur; a coronal plane perpendicular to the transverse plane and tangent to at least one of the posterior-most points of the condyles; a sagittal plane perpendicular to the transverse plane and bisecting the component, the sagittal plane defining a component midline in the coronal plane, the component midline equidistant from a lateral edge of the lateral condyle and a medial edge of the medial condyle; and a patellar groove defining a laterally canted patellar axis when viewed from an anterior side of the component, wherein the patellar axis laterally diverges from the component midline as the patellar axis extends proximally to define a laterally canted angle between the patellar axis and the component midline, the laterally canted angle between about zero degrees and about 4 degrees.

In yet another form thereof, the present invention provides a set of femoral components adapted to mount to a femur having an anatomic axis and a mechanical axis, the femur having lateral and medial condyles with respective distal-most points before resection, the femur defining a mechanical transverse plane normal to the mechanical axis and an anatomic transverse plane tangent to each of the distal-most points, the set comprising: a first femoral component having a first lateral condyle, a first medial condyle opposite the first lateral condyle, such that a path from the first lateral condyle toward the first medial condyle defines a medial direction, and a first anterior flange joining the first lateral condyle to the first medial condyle, the first anterior flange defining a medially canted patellar groove extending in the medial direction as the medially canted patellar groove extends proximally; and a second femoral component having a second lateral condyle, a second medial condyle opposite the second lateral condyle, such that a path from the second medial condyle toward the second lateral condyle defines a lateral direction, and a second anterior flange joining the second lateral condyle to the second medial condyle, the second anterior flange defining a laterally canted patellar groove extending in the lateral direction as the laterally canted patellar groove extends proximally.

In still another form thereof, the present invention provides a femoral component adapted to be mounted to a femur according to a mechanical implantation method or according to an anatomic implantation method, the femur defining a mechanical axis and an anatomic axis, the component having a bone-contacting surface and an opposed articulation surface, the component further having proximal, distal, anterior and posterior portions, the component comprising: a pair of condyles including a medial condyle and a lateral condyle, each of the condyles defining respective distal-most points and posterior-most points; a patellar groove proximate the anterior portion of the component; a transverse plane tangent to each of the distal-most points of the condyles; a coronal plane perpendicular to the transverse plane and tangent to at least one of the posterior-most points of the condyles; a sagittal plane perpendicular to the transverse plane and disposed between the lateral condyle and the medial condyle, the sagittal plane inclusive of a distal-most point of the patellar groove, the sagittal plane including a component midline that is normal to the transverse plane and inclusive of the distal-most point of the patellar groove, the patellar groove defining a medially canted patellar axis when viewed from an anterior side of the component, the patellar axis medially diverging from the component midline as the patellar axis extends proximally to define a medially canted angle between the patellar axis and the component midline, or the patellar groove defining a laterally canted patellar axis when viewed from an anterior side of the component, the patellar axis laterally diverging from the component midline as the patellar axis extends proximally to define a laterally canted angle between the patellar axis and the component midline, the medially or laterally canted patellar axis lying in a plane which intersects a femoral head of the femur, in particular which approximately intersects a center of the femoral head of the femur, when the femoral component is properly mounted to the femur according to the mechanical implantation method or the anatomic implantation method, respectively.

In yet another form thereof, the present invention provides a method of implanting a femoral component onto a distal end of a femur, the method comprising: determining the location of a center of a femoral head of the femur; resecting the distal end of the femur to create a resected distal surface; providing a femoral component comprising a patellar groove proximate an anterior portion of the component, the patellar groove defining a patellar axis when viewed from an anterior side of the component; and implanting the femoral component onto the resected distal surface such that the patellar axis is oriented toward the center of the femoral head, such that the patellar axis substantially intersects the center of the femoral head.

In yet another form thereof, the present invention provides a method of implanting a femoral component onto a distal end of a femur, the method comprising: determining the alignment and orientation of a mechanical axis of the femur; providing a femoral component, the component comprising: a pair of condyles including a medial condyle and a lateral condyle each defining respective distal-most points; a patellar groove proximate an anterior portion of the component, the patellar groove defining a patellar axis as viewed from an anterior side of the component; and implanting the femoral component such that the patellar axis defines a medially canted angle between the patellar axis and the mechanical axis, as projected onto a coronal plane.

In still another form thereof, the present invention provides a method of implanting a femoral component onto a distal end of a femur, the method comprising: determining the alignment and orientation of an anatomical axis of the femur; locating the distal-most points of anatomic femoral condyles of the femur; identifying an anatomic transverse plane that is i) perpendicular to the anatomical axis of the femur from a sagittal view and ii) inclusive of a line connecting the distal-most points of the anatomic femoral condyles; providing a femoral component, the component comprising: a pair of condyles including a medial condyle and a lateral condyle each defining respective distal-most points; a patellar groove proximate an anterior portion of the component, the patellar groove defining a patellar axis as viewed from an anterior side of the component; and implanting the femoral component such that the patellar axis forms a laterally canted angle with respect to a line normal to the anatomic transverse plane, as projected onto a coronal plane.

BRIEF DESCRIPTION OF THE DRAWINGS

The above mentioned and other features and advantages of this invention, and the manner of attaining them, will become more apparent and the invention itself will be better understood by reference to the following description of embodiments of the invention taken in conjunction with the accompanying drawings, wherein:

FIG. 6A is an elevation view of a femur with an attached femoral component, with the femur in an extension position; and FIG. 6B is an elevation view of the femur and femoral component of FIG. 6A, with the femur in a flexion position.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

1. Introduction

The present disclosure provides a prosthetic femoral component for use in an orthopaedic knee prosthesis. The prosthetic femoral component defines a transverse plane tangent to the distal-most points of the prosthesis condyles, referred to herein as the "component transverse plane." The component may be implanted in a "mechanical orientation," in which the component transverse plane is substantially parallel to a plane normal to the mechanical axis of the femur, referred to herein as the "mechanical transverse plane." Femoral components mounted in a mechanical orientation include medially canted patellar grooves, such that the patellar groove diverges medially from a midline bisecting the component as the groove extends proximally.

Alternatively, the component may be implanted in an "anatomical orientation," in which the component transverse plane is substantially parallel to an anteroposterior plane contacting both distal-most points of the natural femoral condyles, referred to herein as the "anatomic transverse plane." Femoral components mounted in an anatomic orientation include either i) laterally canted patellar grooves, such that the patellar groove diverges laterally from a midline bisecting the component as the groove extends proximally, or ii) non-canted grooves, such that the patellar groove does not diverge either medially or laterally from the midline of the component.

In addition to the medial or lateral cant of the patellar groove, the groove may also be "shifted" medially or laterally, as described in detail below. More particularly, the point of intersection of the projection of the patellar groove in a coronal plane (referred to herein as the "patellar axis," as discussed below) with the component transverse plane may be shifted medially or laterally from the component-bisecting midline. This medial or lateral "shift" of the patellar groove can be made independently of the medial or lateral cant of the patellar groove angle.

Advantageously, patellar grooves of femoral components made in accordance with the present disclosure may provide enhanced articular characteristics, including minimized patient discomfort in the anterior knee after knee arthroplasty, minimized risk of patella subluxation during extension and flexion of the knee, and prolonged service life of the prosthetic femoral component and natural or prosthetic patella.

2. Definitions and Lexicon

Figure 1:
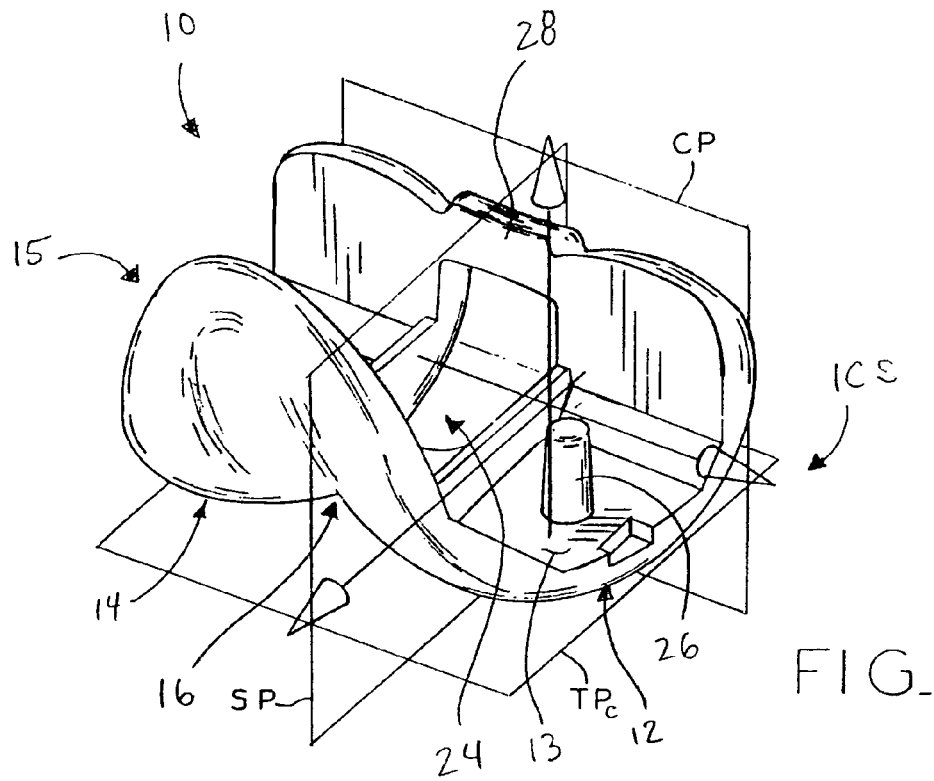
FIG. 1 is a perspective view of a femoral component in accordance with the present disclosure, illustrating the planes of an implant coordinate system.

Referring to FIG. 1, femoral component 10 resides within implant coordinate system ICS including sagittal plane SP, transverse component plane $TP_C$ and coronal plane CP. For purposes of the present disclosure, implant coordinate system ICS is referenced to femur F (FIG. 5) such that planes $TP_C$, SP and CP may be considered fixed in their respective orientations and positions relative to femur F in the manner described below, irrespective of movements in other parts of a patient's body. Transverse plane $TP_C$, coronal plane CP, and sagittal plane SP generally correspond to anatomic transverse, coronal and sagittal planes respectively, but are not necessarily coplanar with same. The specific orientations of planes $TP_C$, CP, SP are defined according to the discussion herein.

Component transverse plane $TP_C$ is tangent to the distal-most points of condyles 12, 14 of femoral component 10, and extends generally mediolaterally and anteroposteriorly. Transverse plane $TP_C$ is perpendicular to anatomic axis AA of femur F when component 10 is properly mounted to femur F (as described below). Moreover, the distal-most points of condyles 12, 14, taken in the abstract, will generally correspond to the distal-most points of condyles 12, 14 with respect to anatomic axis AA when femoral component 10 is mounted to femur F.

While it is contemplated that a surgeon has some flexibility in the manner and method with which femoral component 10 is implanted onto femur F, the actual distal-most points of condyles 12, 14 after component implantation will only vary slightly. For example, the surgeon is limited in making a posterior cut on femur F by the extent to which natural femoral condyles 3, 4 extend posteriorly past the femoral cortex, because the surgeon will traditionally seek to avoid resection of any portion of the femoral shaft. An anterior cut is similarly limited, and is typically nearly parallel to the posterior cut. Finally the distal cut is typically performed to resect no more bone than necessary. In view of these physical constraints on the resection of femur F, any variability in the actual distal-most points of condyles 12, 14 arising from surgeon discretion during implantation of femoral component 10 will have a negligible effect on the overall medial or lateral cant and/or shift. In the illustrated embodiment, transverse plane $TP_C$ is parallel with bone-contacting surface 13 of component 10 (FIGS. 1 and 2), though it is contemplated that surface 13 may have any angular arrangement.

Moreover, a surgeon will recognize, with a high degree of certainty and precision, which points on a prosthetic femoral component will correspond to the distal-most and posterior-most points after implantation. Taken in conjunction with a surgical technique proposed by manufacturers of such components, the location of distal-most and posterior-most points on the component can be determined even more exactly.

Figure 2:
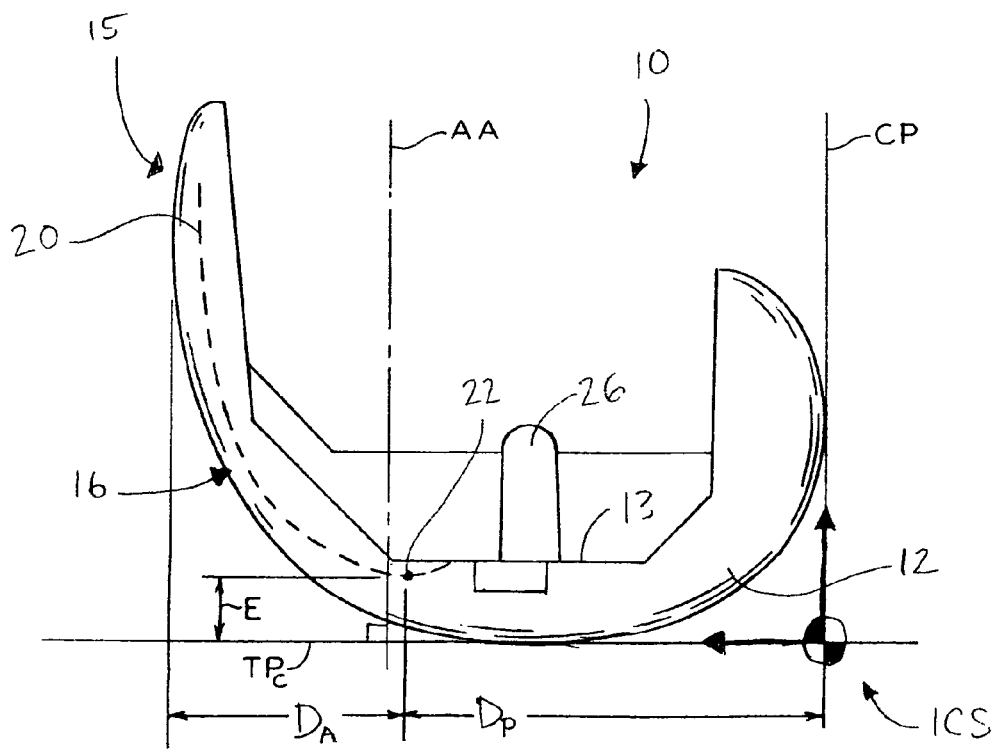
FIG. 2 is a side elevation view of the femoral component shown in FIG. 1, illustrating a trochlear groove projected in a sagittal plane to form a patellar curve.

Coronal plane CP is generally perpendicular to transverse plane $TP_C$ and sagittal plane SP, and is anteroposteriorly positioned to be coincident with at least one posterior-most point on condyles 12, 14 of component 10 (FIG. 2). Coronal plane CP is parallel to anatomic axis AA (described below) of femur F, as illustrated in FIG. 2. When component 10 is properly mounted to femur F (as described below), coronal plane CP generally corresponds to the posterior-most points of the (formerly unresected) natural condyles 3, 4 of femur F.

It is contemplated that coronal plane CP may be defined as an anatomic coronal plane CP or a mechanical coronal plane CP. The anatomic coronal plane CP is tangent to both posterior-most points of condyles 3,4 in a natural knee, and is tangent to the posterior-most points of condyles 12, 14 in a knee which has component 10 implanted. The anatomic plane is therefore inclusive of articular line $L_A$ (FIG. 6A) when the knee is articulated to a 90-degree flexion orientation. The mechanical coronal plane CP is tangent to only one of condyles 3, 4 (or condyles 12, 14) when the knee is flexed to 90-degrees, and is parallel to transverse tibial plane $TP_T$. As described below, transverse tibial plane $TP_T$ is a transverse plane fixed with respect to tibia T and parallel to mechanical transverse plane $TP_M$ when femur F is in the extension position.

Sagittal plane SP is generally perpendicular to transverse plane $TP_C$ and is mediolaterally positioned to bisect condyles 12, 14. In the illustrated embodiment of FIGS. 3 and 4, sagittal plane SP forms midline $L_M$, which is equidistant from the edges of condyles 12, 14 and is normal to component transverse plane $TP_C$. When component 10 is properly mounted to femur F (as described below), condyles 3, 4 are also substantially bisected by sagittal plane SP, so that sagittal plane SP is generally coincident with the "top" or proximal-most point 5 of patello-femoral groove 6 (FIG. 5) of femur F, as viewed in coronal plane CP.

Figure 5:
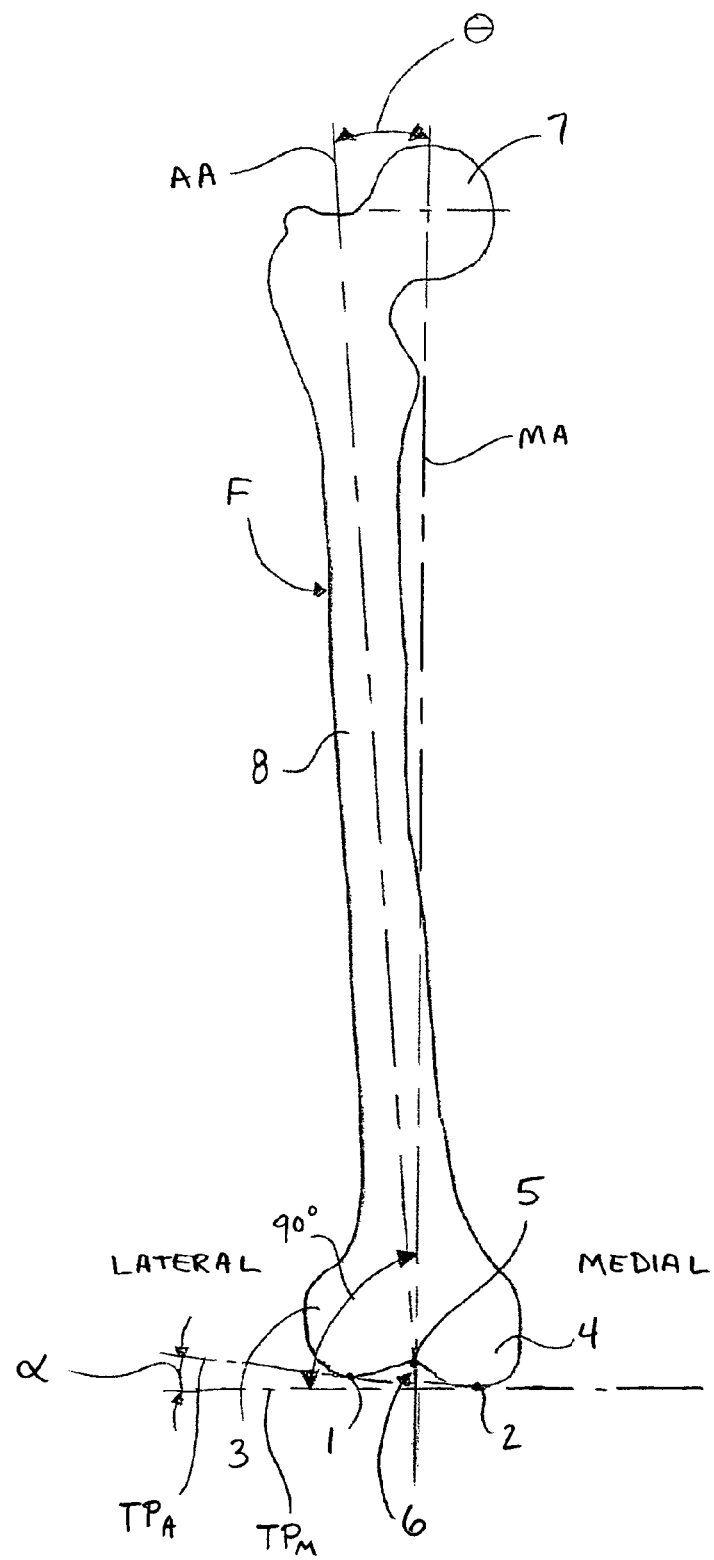
FIG. 5 is an elevation view of a femur, illustrating mechanical and anatomic transverse planes in accordance with the present disclosure.

Referring now to FIG. 5, natural femur F defines mechanical axis MA and anatomical axis AA. Mechanical axis MA extends from the center of femoral head 7 to the center of the knee joint and is the weight bearing axis of femur F. Anatomical axis AA extends along the longitudinal axis of shaft 8 of femur F. A surgeon may find anatomical axis AA by, e.g., obtaining pre-operative images (such as CT scans, magnetic resonance imagining, X-rays or the like) and estimating the longitudinal axis of the shaft of femur F based on sight and appearance. During a surgical procedure, a surgeon may find anatomical axis AA by inserting an intramedullary rod into the intramedullary canal of femur F. Once the rod is so inserted, the axis of the rod is substantially coincident with the axis of femur F. To find mechanical axis MA, a surgeon may again use preoperative images to estimate the location of axis MA by sight. Alternatively, the surgeon may use a rod-based system in conjunction with manipulation of the leg to find axis MA. One exemplary rod-based system and method for finding a mechanical femoral axis is described in U.S. patent application Ser. No. 12/695,804, filed Jan. 28, 2011 and entitled APPARATUS AND METHOD FOR THE EXTRAMEDULLARY LOCATION OF THE MECHANICAL AXIS OF A FEMUR, which is commonly assigned with the present application, the entire disclosure of which is hereby expressly incorporated herein by reference.

Once either mechanical axis MA or anatomical axis AA is determined, a surgeon may infer the location of the other by the knowledge that angle Θ (FIG. 5) separating axes MA, AA is typically about 6 degrees, as viewed in a coronal plane (e.g., the plane of FIG. 5).

Femur F defines two transverse planes, each of which is referenced to different anatomical structures defined by femur F. Mechanical transverse plane $TP_M$ is normal to mechanical axis MA of femur F. In the illustrated embodiment, mechanical transverse plane $TP_M$ is coincident with distal-most point 2 of condyle 4, though other vertical locations are contemplated.

The other transverse plane of femur F is anatomic transverse plane $TP_A$, which includes a line extending from distal-most point 1 of lateral condyle 3 to distal-most point 2 of medial condyle 4 and is perpendicular to coronal plane CP. As noted below, coronal plane CP is parallel to anatomic axis AA of femur F, so that anatomic transverse plane $TP_A$ is perpendicular to anatomic axis AA from a sagittal perspective. Alternatively, anatomic transverse plane $TP_A$ may be defined as a plane tangent to distal-most points 1, 2 of condyles 3, 4. For the above methods of defining plane $TP_A$, distal-most points 1, 2 may be defined as the distal-most points on an undamaged femur F. In yet another alternative, transverse plane $TP_A$ may be defined as having a fixed angle with mechanical transverse plane $TP_M$, with the fixed angle chosen to render plane $TP_A$ nearly tangent to distal-most points 1, 2 for a statistically substantial portion of the patient population (i.e., based on analysis of empirical patient data).

In an exemplary embodiment, resection of femur F may leave a distal resected surface parallel to mechanical transverse plane $TP_M$ to facilitate a "mechanical orientation" of component 10 after implantation. Such a "mechanical" resection allows the use of a femoral component with uniform thickness between distal bone-contacting surface and the articular surfaces of both medial condyle 12 and lateral condyle 14. On the other hand, resection of femur F may leave a distal resected surface parallel to anatomic transverse plane $TP_A$. Such "anatomic" resection facilitates an "anatomic orientation" of a component having similarly constant condylar thickness. However, it is contemplated that any resection may be used with a femoral component made in accordance with the present disclosure, as required or desired for a particular design.

Referring still to FIG. 5, femur F defines anatomic varus/valgus angle α within the context of implant coordinate system ICS. For purposes of the present disclosure, anatomic varus/valgus angle α is the angle between mechanical transverse plane $TP_M$ and anatomic transverse plane $TP_A$. Angle α forms a basis for establishing and/or categorizing variation among natural femurs, particularly within respective gender populations. The variation of anatomic varus/valgus angle α is a factor in determining the degree of medialization or lateralization of patellar femoral groove 16 in femoral component 10.

Turning back to FIGS. 1 and 2, femoral component 10 includes patellar groove 16, which defines patellar axis 18 (FIGS. 3 and 4) and patellar curve 20 (FIG. 2). Patellar axis 18 and patellar curve 20 are projections of a "valley line" formed along the "deepest" part of the valley-like concavity formed by patellar groove 16, i.e., the line formed by the points within patellar groove 16 that are furthest from the outside surface of component 10. This "valley line" is projected onto coronal plane CP to create patellar axis 18, and onto sagittal plane SP to create patellar curve 20.

Figure 3:
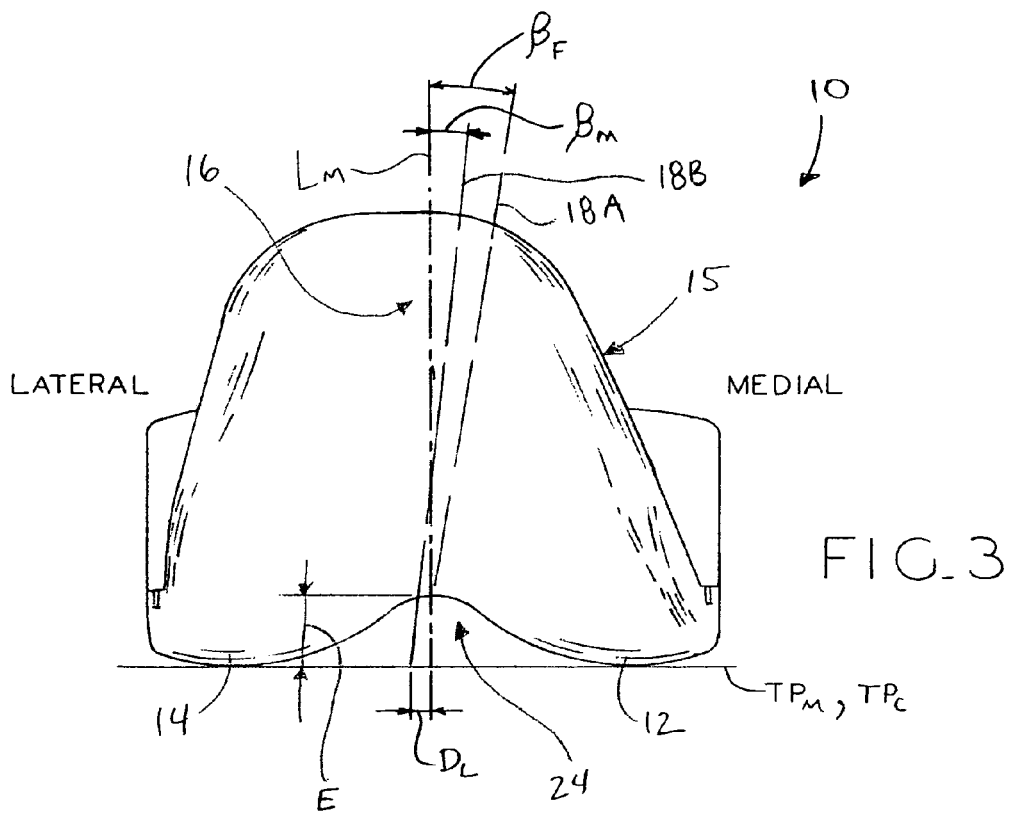
FIG. 3 is a front elevation view of a femoral component adapted to be aligned with a mechanical transverse plane in accordance with the present disclosure.
Figure 4:
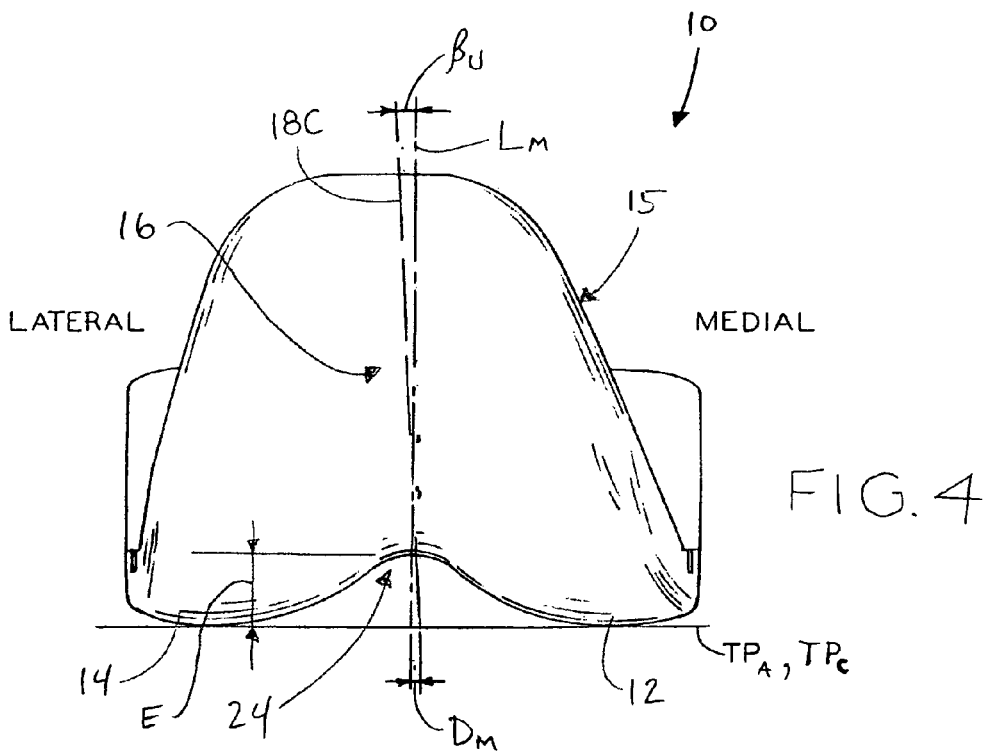
FIG. 4 is a front elevation view of a femoral component adapted to be aligned with an anatomic transverse plane in accordance with the present disclosure.

Referring to FIGS. 3 and 4, patellar axis 18 has a generally linear profile, though it is contemplated that patellar axis 18 may be non-linear as required or desired for a particular design. Patellar axis 18 may be medially or laterally canted and/or shifted, as discussed in detail herein, for particular applications. In an exemplary embodiment, described below, the location and orientation of patellar axis 18 may be varied for gender- and/or ethnicity-specific applications.

Referring to FIG. 2, patellar curve 20 has a generally "J" shape including distal-most point 22, which is the point having a minimum elevation E from component transverse plane $TP_C$ to patellar curve 20 when femoral component 10 is mounted to femur F. Distal-most point 22 defines anteroposterior distance $D_A$, which is the distance from point 22 to the anterior-most point on femoral component 10. Similarly, distal-most point 22 defines anteroposterior distance $D_P$, which is the distance from point 22 to the posterior-most point on femoral component 10 (i.e., coronal plane CP in the illustrated embodiment of FIG. 2).

3. Femoral Component Construction

Referring again to FIG. 1, femoral component 10 includes medial condyle 12, lateral condyle 14 and anterior flange 15. A plurality of bone-contacting surfaces, including distal bone-contacting surface 13, are formed along the inner periphery of component 10. Disposed generally opposite the bone-contacting surfaces, at the exterior periphery of component 10 are articular surfaces. For example, condyles 12, 14 include distal and posterior articular surfaces for articulation with a natural tibia or prosthetic tibial component. These articular surfaces can have any geometry and shape as required or desired for a particular application.

Anterior flange 15 includes patellar groove 16, which forms the anterior articular surface of component 10 for articulation with a natural or prosthetic patella. Patellar groove 16 extends from a generally anterior and proximal starting point to a generally posterior and distal terminus. Patellar groove 16 is adapted to articulate with a natural patella or prosthetic patellar component during the early stages of knee flexion, after which the patella articulates with the inner surfaces of condyles 12, 14 near intercondylar fossa 24. For purposes of the present disclosure, the posterior and distal end of patellar groove 16 generally coincides with the anterior terminus of intercondylar fossa 24 formed between medial and lateral condyles 12, 14. Because a natural or prosthetic patella articulates with the inner surfaces of condyles 12, 14 in deep flexion, however, patellar groove 16 may be said to extend into the distal portion of femoral component 10 near intercondylar fossa 24.

In the illustrated embodiment, femoral component 10 further includes fixation pegs 26 and posterior cam 28 in accordance with a "posterior stabilizing" femoral component design. However, it is contemplated that these structures may be eliminated or modified as required or desired for a particular application such as, for example, a "cruciate retaining" femoral component design with no posterior cam.

Femoral component 10 has several potential configurations to accommodate and account for natural variation among femurs of different patients. Such variations may arise from different bone sizes and geometries, and correspondingly different natural knee articulation characteristics, among patients of different gender, size, age, ethnicity, build or the like. In addition, the configuration of femoral component 10, and particularly of patellar groove 16, may be varied to account for and/or correct varus or valgus deformities in a particular patient.

As illustrated in FIG. 3, femoral component 10 includes patellar groove 16 which may define either medially canted female patellar axis 18A or medially canted male patellar axis 18B, depending on whether femoral component 10 is configured for use with a male or female patient. Medially canted female patellar axis 18A defines angle $\beta_F$ with respect to component midline $L_M$ (described above), while medially canted male patellar axis 18B defines angle $\beta_M$ with respect to component midline $L_M$. As shown in FIG. 3 and described above, axes 18A, 18B are "medially canted" in that they diverge medially from component midline $L_M$ as these axes 18A, 18B extend proximally. The embodiment of femoral component 10 illustrated in FIG. 3 is appropriate for a "mechanical" component orientation, i.e., where component transverse plane $TP_C$ is substantially parallel to and/or coincident with mechanical transverse plane $TP_M$ (FIG. 5) after femoral component 10 is implanted. In an exemplary embodiment of such a "mechanical implantation," femur F may be prepared to receive femoral component 10 by resecting at least the distal portions of natural condyles 3, 4 to form a resected surface substantially parallel to mechanical transverse plane $TP_M$. However, it is contemplated that the resected surfaces of femur F may have any orientation relative to mechanical transverse plane $TP_M$, with the bone-contacting surfaces of component 10 (such as distal bone-contacting surface 13) adjusted to effect the desired mechanical orientation of component 10 after implantation.

For a female patient with a mechanically oriented femoral component 10 (FIG. 3, and as described above), femoral component 10 includes patellar groove 16 defining female medially canted patellar axis 18A forming angle $\beta_F$ with component midline $L_M$ in coronal plane CP. In an exemplary embodiment, angle $\beta_F$ may be any angle between as little as about 3° and as much as about 7°. In the illustrative embodiment of FIG. 3, $\beta_F$ is about 6.8°. Advantageously, a value of about 6.8° for angle $\beta_F$ provides an optimized patella/femur interaction between a natural or prosthetic patella and patellar groove 16 for a large population of female patients.

For a male patient with a mechanically oriented femoral component 10 (FIG. 3), femoral component 10 includes patellar groove 16 defining male medially canted patellar axis 18B, which forms angle $\beta_M$ between male medially canted patellar axis 18B and component midline $L_M$. In an exemplary embodiment, angle $\beta_M$ is generally smaller than the corresponding angle $\beta_F$ for a female patient, though male medial cant angle $\beta_M$ may also be as little as about 3° and as much as about 7°. In the illustrative embodiment of FIG. 3, $\beta_M$ is about 4.5°. Similarly to the value of 6.8° for angle $\beta_F$, a value of 4.5° for angle $\beta_M$ provides an optimized patella/femur interaction between a natural or prosthetic patella and patellar groove 16 for a large population of male patients.

Referring again to FIG. 4, for an anatomically oriented femoral component 10, male and female components made in accordance with the present disclosure may have the same patellar axis/mechanical axis angle. In FIG. 4, femoral component 10 is configured to be implanted on to femur F in an anatomic orientation (i.e., "anatomically implanted"), and includes patellar groove 16 defining laterally canted patellar axis 18C. Laterally canted patellar axis 18C is angled such that axis 18C diverges laterally from component midline $L_M$ as axis 18C extends proximally.

A gender-neutral or "universal" angle $\beta_U$ may be formed between laterally canted patellar axis 18C and component midline $L_M$ when femoral component 10 is configured for an anatomic implantation. The universality of angle $\beta_U$ is made possible because a desirable articulation profile between a natural or prosthetic patella and patellar groove 16 of femoral component 10 has been found to be relatively angle-independent for both male and female patients. More particularly, the optimal angle between axis 18 and mechanical axis MA is only slightly variable for males versus females (as discussed in detail below), with the variation being small enough to enable femoral component 10 to have the same laterally canted patellar axis for both male and female components without compromising the fit, function or other advantages conferred by pairing laterally canted patellar axis 18C of femoral component 10 with an anatomical orientation upon implantation of component 10. In an exemplary embodiment, $\beta_U$ may be as little as 0° (i.e., patellar groove 16 defines a patellar axis 18C that is parallel to, or coincident with, component midline $L_M$) and as much as 4°, for example. In the illustrative embodiment of FIG. 4, $\beta_U$ is about 2°.

The gender neutrality of component 10 with a laterally canted patellar groove 16 is related to anatomic varus/valgus angle α. As discussed above, angle α is the angular disparity between mechanical transverse plane $TP_M$ and anatomic transverse plane $TP_A$, and is measured in an extension orientation of the knee. Thus, referring to FIG. 5, angle α can be thought of as the angle between a line tangent to the articular surfaces of condyles 3, 4 (which, in extension, are also distal-most points 1, 2) and mechanical transverse plane $TP_M$.

However, α is also a relevant angular value throughout flexion of the knee when component 10 is mounted to femur F in an anatomic orientation. Referring now to FIGS. 6 and 6A, articular line $L_A$ forms angle α with transverse tibial plane $TP_T$, which is a transverse plane fixed to tibia T and parallel to mechanical transverse plane $TP_M$ when femur F is in the extension position. Articular line $L_A$ is tangent to the articular surfaces of condyles 12, 14 at the articular interface between component 10 and tibia T (or a tibial component, not shown) at a given degree of flexion. In extension, articular line $L_A$ is coincident with component transverse plane $TP_C$, as shown in FIG. 6A. As the knee flexes, articular line $L_A$ shifts posteriorly along the articular surfaces of condyles 12, 14. As shown in FIG. 6B, for example, articular line $L_A$ has shifted to the posterior-most points of femoral component 10 as the knee has flexed to approximately 90 degrees. However, the angle between articular line $L_A$ and transverse tibial plane $TP_T$ remains unchanged (i.e., equal to angle α). This lack of angular change throughout flexion has been found to mimic articulation characteristics of the natural knee. Moreover, the anatomic implantation of femoral component 10 cooperates with the slight lateral cant of patellar axis 18C to render component 10 gender neutral.

In view of the general concept underlying the present disclosure and as explained above, it may be noted that the anatomic varus/valgus angle α is at least roughly related to certain values of the cant angles as disclosed herein and which have found to be advantageous. Specifically, it has been found that the average sum of an advantageous medial cant angle (e.g. approximately between 3 degrees and 7 degrees) and an advantageous lateral cant angle (e.g. approximately between zero degrees and 4 degrees) corresponds roughly to an anatomic varus/valgus angle α. Exemplary embodiments of femoral component 10 include medially or laterally canted patellar grooves 18A, 18B, 18C which correspond to one such average sum equal to about 7 degrees. These exemplary components represent an ideal prosthesis/anatomy match that is expected to correspond to the largest possible proportion of anatomic structures found among patient populations.

Referring back to FIG. 2, patellar curve 20 includes distal-most point 22 defining elevation E between component transverse plane $TP_C$ and distal-most point 22. In addition, distance $D_A$ is defined between distal-most point 22 and the anterior face of anterior flange 15, while posterior distance $D_P$ is defined between distal-most point 22 and the posterior face of medial and/or lateral condyles 12, 14.

It is contemplated that other characteristics of femoral component 10 may vary depending on whether femoral component 10 is adapted for an anatomic or mechanical implantation. For example, it is contemplated that elevation E may be smaller for femoral component 10 adapted for anatomic implantation (FIG. 4) as compared to femoral component 10 adapted for mechanical implantation (FIG. 3). Further, anterior flange 15 of femoral components 10 adapted for anatomic implantation may be less high and less broad, i.e. generally smaller, when viewed from an anterior side (as in FIGS. 3 and 4), as compared to femoral components adapted for mechanical implantation.

In addition to the medial or lateral cant of patellar axis 18 (which may be one of patellar axes 18A, 18B and 18C, as noted above), patellar axis 18 may also be medially or laterally shifted or "translated" on anterior flange 15 of femoral component 10. For example, referring to FIG. 3, male medially canted patellar axis 18B defines lateral shift distance $D_L$, which is the distance, as measured in coronal plane CP, between component midline $L_M$ and the point where medially canted axis 18B intersects component transverse plane $TP_C$.

In an exemplary embodiment, lateral shift distance $D_L$ may be between 0 and about 4 mm, for example, depending upon the desired location of axis 18B and on the particular characteristics of femoral component 10, such as implant size, implant thickness, and the like. Although lateral shift distance $D_L$ is illustrated with respect to male medially canted patellar axis 18B of femoral component 10, it is contemplated that other configurations of femoral component 10 may have other configurations of patellar axis 18 that are laterally shifted to define lateral shift distance $D_L$, i.e., medially canted patellar axis 18A or laterally canted patellar axis 18C.

On the other hand, the illustrative embodiment of FIG. 4 includes laterally canted patellar axis 18C defining medial shift distance $D_M$, which is the distance, as measured in coronal plane CP, between component midline $L_M$ and the point where laterally canted axis 18C intersects anatomic transverse plane $TP_A$. In an exemplary embodiment, medial shift distance $D_M$ may be between 0 mm and about 4 mm, for example, depending upon the desired location of axis 18C and on the particular characteristics of femoral component 10 such as implant size, implant thickness, and the like. Similar to lateral shift distance $D_L$, medial shift distance $D_M$ may be defined by any of medially canted or laterally canted patellar axes 18A, 18B, or 18C.

Although femoral component 10 is described above as being a single component having several varying configurations, it is contemplated that a set or kit of femoral components 10 may be provided for use in either a mechanical or anatomic orientation of component 10 after implantation thereof. Each kit may include a plurality of implant sizes for various different sizes of femur F, as may be encountered in various individual patients. In the case of femoral component 10 adapted for use in a mechanical implantation, a first full set or kit may be provided for female patients, while a second full set or kit may be provided for male patients. These two gender-specific kits are provided because femoral component 10 is configured differently for male and female patients when mechanically oriented (i.e., femoral component 10 includes either male medially canted patellar axis 18A or female medially canted patellar axis 18B, as shown in FIG. 3 and discussed above).

On the other hand, where femoral component 10 has lateralized patellar axis 18C adapted for use in an anatomic implantation, a single kit may be provided for both male and female patients. This single, gender-neutral kit of anatomically oriented components will generally include a larger number of components as compared to a gender-specific kit of mechanically-oriented component, because the gender-neutral kit will include a wider range of component sizes to accommodate the size disparities between male and female femur populations.

Advantageously, femoral components made in accordance with the present disclosure may be provided as kits or sets which are gender specific, particularly where a mechanical implantation is intended, while also integrating any number of other technologies and features now known or later discovered. Moreover, a patellar groove in accordance with the present disclosure may be integrated into a wide range of other existing femoral component designs, such that the components offer the benefits of a medially canted or laterally canted patellar groove 16 as described above, while also providing other unique features, articular characteristics and/or kinematic profiles. Thus, the patello-femoral benefits and advantages, discussed above, may be obtained for a wide variety of patient populations while also benefitting from other orthopaedic technologies such as particular condyle designs, component affixation designs and methods, advanced materials, and the like.

Also advantageously, femoral components 10 are adapted to be implanted in mechanical and anatomic orientations, respectively, to substantially reproduce or mimic the natural kinematic profile of healthy femur/patella interaction in a natural knee. As described below, analysis of healthy patient patellar grooves and other characteristics of healthy patient femurs confirms that a medially canted patellar axis, used in conjunction with a mechanical implantation of femoral component 10, can be used to achieve enhanced articular characteristics (such as, for example, patello-femoral articular characteristics) in a knee prosthesis. Similarly, this analysis further confirms that enhanced articular characteristics can be gained from the use of femoral components having a laterally canted patellar axis in conjunction with an anatomic implantation of femoral component 10. In each case, femoral components made in accordance with the present disclosure have been found to produce desirable articular characteristics while using a patellar groove that is canted and/or oriented in a manner contrary to conventional wisdom in the art of orthopaedic femoral prostheses.

Advantageously, the enhanced patello-femoral joint articulation provided by femoral component 10 may include, among other benefits: minimized anterior knee pain following a TKA procedure; maintenance of appropriate tension in the retinaculum, thereby minimizing risk to same during surgical procedures; promotion of appropriate/optimum intraoperative surgical decisions regarding the relative size and geometry of the lateral femoral condyle; minimization or elimination of external rotation of the femoral component with respect to the femur; minimized risk of patella subluxation during articulation of the knee prosthesis, particularly at extreme extension and extreme flexion ranges of motion; and greater longevity of components in the knee prosthesis, such as femoral component 10, a natural or prosthetic patella and/or a tibial component, for example.

Yet another advantage of femoral component 10 in accordance with the present disclosure is that the articulation between a natural or prosthetic patella and patellar groove of femoral component 10 facilitates femoral lateral rollback in deep flexion.

A procedure to mount femoral components 10 with medially canted patellar axes 18A or 18B to femur F will now be described. Prior to resection of femur F, the alignment and orientation of mechanical axis MA and anatomical axis AA for femur F is determined and noted. A resection is performed using conventional methods and instruments. In an exemplary embodiment, the resection creates a distal cut surface normal to mechanical axis MA (and, concomitantly, parallel to mechanical transverse plane $TP_M$), though other cut geometries may be used. Corresponding anterior, posterior, anterior chamfer and/or posterior chamfer cuts are also made as necessary.

The surgeon then provides femoral component 10 for implantation onto femur F. As used herein, "providing" femoral component 10 refers to procurement thereof, such as from a kit or operating-room container or storage receptacle. Prior to the step of providing component 10, the surgeon may or may not be involved with acquisition from the manufacturer, receipt of shipments, inventorying, or other procurement activities occurring outside the operating room environment.

Femoral component 10 having one of medialized groove 18A or 18B (depending on the gender of the patient, as described herein) is then mounted to femur F so that component transverse plane $TP_C$ is parallel to and/or coincident with mechanical transverse plane $TP_M$. The fixation of femoral component 10 to femur F is accomplished using conventional fixation methods and structures, such as bone cement, bone-ingrowth material and/or fixation pegs 26, for example. A prosthetic patellar component may also be implanted to cooperate with femoral component 10, or the natural patella may be retained for such articulation. Range of motion may be analyzed, including observation and analysis of patello-femoral kinematic and articular characteristics. When the surgeon is satisfied with the location and placement of femoral component 10 and any other associated components of the knee prosthesis, surgery is completed in accordance with conventional methods.

The procedure to mount femoral components 10 with laterally canted patellar axes 18C to femur F is similar to the corresponding procedure for components 10 with medially canted patellar axes 18A, 18B described above. However, rather than selecting component 10 with medially canted axes 18A, 18B and implanting such component 10 so that component transverse plane $TP_C$ is parallel to and/or coincident with mechanical transverse plane $TP_M$, component 10 is selected with laterally canted patellar axis 18C and is implanted such that component transverse plane $TP_C$ is parallel to and/or coincident with anatomic transverse plane $TP_A$, as described above.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A femoral component adapted to mount to a femur, the femur defining a mechanical axis and an anatomic axis, the component defining a component coordinate system having:
    a component transverse plane;
    a coronal plane perpendicular to said component transverse plane;
    a sagittal plane perpendicular to said component transverse plane and including a component midline that is normal to said component transverse plane;
    the component having a bone-contacting surface and an opposed articulation surface, the component further having proximal, distal, anterior and posterior portions, the component comprising:
    a pair of condyles including a medial condyle and a lateral condyle, each of said condyles defining respective distal-most points and posterior-most points, said component transverse plane tangent to each of said distal-most points, said coronal plane tangent to at least one of said posterior-most points, and said sagittal plane disposed between said lateral condyle and said medial condyle; and
    a patellar groove proximate the anterior portion of the component, said component midline of said sagittal plane inclusive of a distal-most point of said patellar groove, said patellar groove extending from said distal-most point toward an anterior-most edge of said femoral component,
    said patellar groove defining a medially canted patellar axis when viewed from an anterior side of said component, said patellar axis medially diverging from said component midline as said patellar axis extends proximally to define a medially canted angle between said patellar axis and said component midline.

2. The femoral component of claim 1, wherein said medially canted angle comprises an angle between about 3 degrees and about 7 degrees.

3. The femoral component of claim 1, wherein said femoral component comprises a femoral component sized and shaped for a male patient, and said medially canted angle comprises an angle that is about 4.5 degrees.

4. The femoral component of claim 1, wherein said femoral component comprises a femoral component sized and shaped for a female patient, and said medially canted angle comprises an angle that is about 6.8 degrees.

5. The femoral component of claim 1, wherein said component midline and said patellar axis intersect the component transverse plane at a common point.

6. The femoral component of claim 1, wherein said component midline and said patellar axis intersect the component transverse plane at a pair of different points spaced from one another by a mediolateral distance,
    in particular said mediolateral distance between zero mm and 4 mm.

7. The femoral component of claim 1, wherein said patellar axis extends straight from said distal-most point to said anterior-most edge of said femoral component.

8. The femoral component of claim 1, wherein said component transverse plane is substantially perpendicular to said femur mechanical axis.

9. A set of femoral components adapted to mount to a femur having an anatomic axis and a mechanical axis, the femur having lateral and medial condyles with respective distal-most points before resection, the femur defining a mechanical transverse plane normal to the mechanical axis and an anatomic transverse plane tangent to each of said distal-most points, the set comprising:
    a first femoral component having
        a first lateral condyle,
        a first medial condyle opposite said first lateral condyle, such that a path from said first lateral condyle toward said first medial condyle defines a medial direction, and
        a first anterior flange joining said first lateral condyle to said first medial condyle, said first anterior flange having a patellar groove defining a medially canted patellar axis extending in said medial direction as said medially canted patellar groove extends proximally; and
    a second femoral component having
        a second lateral condyle,
        a second medial condyle opposite said second lateral condyle, such that a path from said second medial condyle toward said second lateral condyle defines a lateral direction, and
        a second anterior flange joining said second lateral condyle to said second medial condyle, said second anterior flange having a patellar groove defining a laterally canted patellar axis extending in said lateral direction as said laterally canted patellar groove extends proximally,
    said first lateral and medial condyles and said second lateral and medial condyles each defining respective distal-most points and respective posterior-most points, each of said first femoral component and said second femoral component defining a component coordinate system having:
    a component transverse plane tangent to each of said distal-most points;

a coronal plane perpendicular to said component transverse plane and tangent to at least one of said posterior-most points; and a sagittal plane perpendicular to said component transverse plane and disposed between said first lateral condyle and said first medial condyle, said sagittal plane inclusive of a distal-most point of said patellar groove, said sagittal plane including a component midline that is normal to said component transverse plane and inclusive of said distal-most point of said patellar groove, said medially canted patellar axis of said medially canted patellar groove of said first anterior flange defining a medially canted angle with respect to said component midline, when viewed from an anterior side of said first femoral component, and said laterally canted patellar axis of said laterally canted patellar groove of said second anterior flange defining a laterally canted angle with respect to said component midline, when viewed from an anterior side of said second femoral component.

10. The femoral component of claim 9, wherein said medially canted angle comprises an angle between about 3 degrees and about 7 degrees.

11. The femoral component of claim 9, wherein said first femoral component comprises a femoral component sized and shaped for a male patient, and said medially canted angle comprises an angle that is about 4.5 degrees.

12. The femoral component of claim 9, wherein said first femoral component comprises a femoral component sized and shaped for a female patient, and said medially canted angle comprises an angle that is about 6.8 degrees.

13. The femoral component of claim 9, wherein said second femoral component is one of a male and female femoral component, and said laterally canted angle is about 2 degrees.

14. The femoral component of claim 9, wherein said second femoral component comprises a gender-neutral femoral component.

15. The femoral component of claim 9, wherein:

said medially canted patellar groove of said first anterior flange extends from said distal-most point of said patellar groove straight toward an anterior-most edge of said first femoral component; and said laterally canted patellar groove of said second anterior flange extends from said distal-most point of said patellar groove straight toward an anterior-most edge of said second femoral component.

16. The femoral component of claim 9, wherein:

said component transverse plane of said first femoral component is substantially perpendicular to said femur mechanical axis; and said component transverse plane of said second femoral component is substantially perpendicular to said femur anatomical axis.

\* \* \* \* \*